United States Patent [19]

Hagiya et al.

[11] Patent Number: 4,948,914
[45] Date of Patent: Aug. 14, 1990

[54] PROCESS FOR PREPARING TRANS-2,2-DIMETHYL-3-(2,2-DIHALOVINYL)CYCLOPROPANE CARBOXYLIC ACID ESTERS

[75] Inventors: Koji Hagiya; Gohfu Suzukamo, both of Osaka; Masami Fukao, Shiga, all of Japan; Yoji Sakito, Montreal, Canada; Hiroko Sakane, Osaka, Japan

[73] Assignee: Sumitomo Chemical Co., Limited, Osaka, Japan

[21] Appl. No.: 352,288

[22] Filed: May 16, 1989

[30] Foreign Application Priority Data

May 26, 1988 [JP] Japan .................. 63-128626
Aug. 9, 1988 [JP] Japan .................. 63-199157

[51] Int. Cl.$^5$ .................. C07C 69/743
[52] U.S. Cl. .................. 560/124
[58] Field of Search .................. 560/124

[56] References Cited

U.S. PATENT DOCUMENTS

| | | | |
|---|---|---|---|
| 3,794,680 | 2/1974 | Matsui | 560/124 |
| 4,473,703 | 9/1984 | Suzukamo | 560/124 |
| 4,788,323 | 11/1988 | Suzukamo | 560/124 |
| 4,820,864 | 4/1989 | Suzukamo | 560/124 |

FOREIGN PATENT DOCUMENTS 2539895 3/1976 Fed. Rep. of Germany.
2716771 11/1977 Fed. Rep. of Germany.
2716773 11/1977 Fed. Rep. of Germany.

*Primary Examiner*—Michael L. Shippen
*Attorney, Agent, or Firm*—Birch, Stewart, Kolasch & Birch

[57] ABSTRACT

Trans-2,2-dimethyl-3-(2,2-dihalovinyl)-cyclopropane carboxylic acid esters which are intermediate of insecticides are prepared by allowing (1) alkali metal alkoxides and titanium alkoxides or (2) silicon iodides to react with cis- or cis-/trans-mixed 2,2-dimethyl-3-(2,2-dihalovinyl)-cyclopropane carboxylic acid esters of the formula

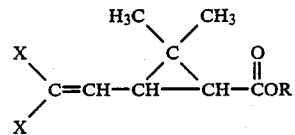

wherein X is a halogen atom and R is an alkyl, cycloalkyl or aralkyl group having 1–10 carbon atoms.

17 Claims, No Drawings

PROCESS FOR PREPARING TRANS-2,2-DIMETHYL-3-(2,2-DIHALOVINYL)CYCLOPROPANE CARBOXYLIC ACID ESTERS

The present invention relates to a process for preparing trans-2,2-dimethyl-3-(2,2-dihalovinyl)-cyclopropane carboxylic acid esters having the formula

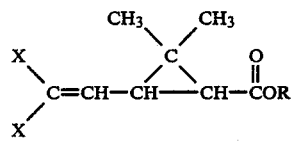

where X stand for a halogen atom and R stands for an alkyl, cycloalkyl or aralkyl group having 1-10 carbon atoms.

2,2-Dimethyl-3-(2,2-dihalovinyl)-cyclopropane carboxylic acid (hereinafter referred to as dihalo acid) is an acid moiety of permethrin, cypermethrin, etc., insecticides which are familiar as household ones and are strongly active against agricultural or forest pests. Dihalo acid esters are useful for intermediates of these insecticides.

Dihalo acid has geometrical isomers, cis and trans, on the basis of a cyclopropane ring. It has been known that, in general, among the isomers the esters derived from trans-isomers are less toxic against mammals than those derived from cis isomers (Nature 244, 456, 1973). Dihalo acid esters are industrially produced by allowing 1,1-dihalo-4-methyl-1, 3- pentadiene to react with diazoacetate but the product esters are in the form of a mixture of trans- and cis-isomers. Accordingly, it is a problem to convert cis-isomers to trans-isomers, particularly in a commercial scale. Alkali metal alkoxide is used for the conversion of cis alkyl chrysanthemate to trans-form where the symbol X is methyl group in the formula (I) (Japanese Patent Kokoku 56-12625). However, this process is not suitable for &he dihalo acid esters, since the conversion rarely proceeds or often accompanies dehydrohalogenation in the dihalovinyl group (Tetrahedron Letters, 23, 5003, 1982). Another process for the conversion is to irradiate cis-dihalo acid esters with light in the presence of photosensitizers (Japanese Patent Kokai 52-5738). This process is not economical, since a large amount of energy is needed and the reaction reaches photo stationary state at the level of 4/6 of cis/trans ratio in the product produced.

After an extensive study, the present inventors succeeded in finding the fact that (1) alkali metal alkoxides together with titanium alkoxides or (2) silicon iodide causes the conversion to proceed more smoothly and selectively. The present invention is established on the basis of the above finding to which some additional research is made.

According to the present invention, an efficient process for preparing trans-2,2-dimethyl-3-(2,2-dihalovinyl)-cyclopropane carboxylic acid esters is provided, i.e., a process wherein (1) alkali metal alkoxides together with titanium alkoxides or (2) silicon iodides are allowed to react with cis- or cis/trans-mixed 2,2-dimethyl-3-(2,2-dihalovinyl)-cyclopropane carboxylic acid esters of the formula

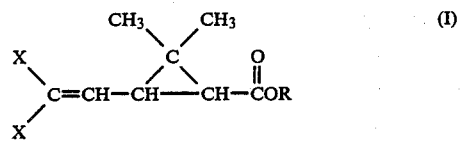

wherein X stands for halogen atoms, and R stands for an alkyl, cycloalkyl or aralkyl group having 1-10 carbon atoms.

Dihalo acid esters (I), the starting compound in the present process, include, for example, esters of dichloro acids, dibromo acids, difluoro acids or chlorofluoro acids. They are, for example, esters with alkyl, cycloalkyl or aralkyl groups having 1-10 carbon atoms such as methyl, ethyl, propyl, butyl, cyclohexyl, cyclohexylmethyl or benzyl groups, preferably ethyl ester.

Dihalo acid esters may be in the form of cis-isomers alone or any mixture of cis-isomers and trans-isomers. Preferable are cis-isomers alone or mixtures rich in cis-isomers.

Reaction in the presence of alkali metal alkoxides and titanium alkoxides

Alkali metals of the alkali metal alkoxides are lithium, sodium and potassium. Alkoxides are methoxide, ethoxide, n-propoxide, iso-propoxide, t-butoxide, sec-butoxide, iso-butoxide, pentanoxide or hexanoxide. Preferable alkali metal alkoxides are lithium or sodium alkoxides, more preferably, lithium ethoxide, lithium propoxide, sodium ethoxide and sodium propoxide. They are used usually in an amount of 1/50-1 time, preferably 1/20-½ time as much as dihalo acid esters in mole.

Titanium alkoxides are, for example, titanium methoxide, titanium ethoxide, titanium propoxide, titanium isopropoxide, titanium butoxide, titanium isobutoxide, titanium sec-butoxide or titanium t-butoxide. They are used usually in an amount of 1/50-½ time, preferably 1/20-1/5 time as much as dihalo acid esters, in mole.

The conversion is usually conducted in such a manner that dihalo acid esters are mixed with titanium alkoxides in the absence or presence of inert solvents and then alkali metal alkoxides are mixed therewith. The reaction is usually conducted at 50°-200° C., preferably 100°-150° C., although the temperature varies depending on amounts and kinds of titanium alkoxides and alkali metal alkoxides employed. The reaction is usually effected for 1-15 hours, although the reaction time varies depending on amounts and kinds of titanium alkoxides and alkali metal alkoxides employed, too.

Reaction in the presence of silicon iodide

The convenient silicon iodide is silicon tetraiodide. It is usually used in an amount of 1/50 -1 time, preferably 1/25 ½ time as much as dihalo acid esters in mole.

The conversion reaction proceeds more smoothly in the presence of 1/200-1 time, preferably 1/100-1/5 time of iodine halides as much as dihalo acid esters, in mole. The iodine halides are, for example, iodine, iodine monobromide, iodine monochloride or iodine trichloride.

Conversion reaction in the presence of silicon iodides is usually carried out in the presence of inert organic solvent. They are, for example, aromatic hydrocarbons such as benzene, toluene, xylene, cumene, trimethylbenzene or nitrobenzene; halogenated hydrocarbons such as chloroform, carbon tetrachloride, dichloroethane, chlorobenzene, o-dichlorobenzene or bromobenzene; or nitriles such as acetonitrile, propionitrile or butyronitrile, preferably halogenated hydrocarbons or nitriles.

The reaction is usually conducted in such a manner that the dihalo acid esters are dissolved in the solvents and then silicon iodides are added thereto before iodinehalides, if employed, are added.

Reaction temperature is usually 0°–150° C., preferably 15°–150° C., although it varies depending on amounts of silicon iodides and iodine-halides employed and kinds of solvents. Reaction time is usually 0.5–15 hours, although it varies depending on amounts and kinds of silicon iodides, iodine-halides and solvents employed.

Isolation of the reaction product

Progress of the reaction may be checked by analysing a portion of reaction mixture with gas chromatography, NMR or IR spectroscopy. After the catalyst is removed from a reaction mass, the desired ester compound is isolated by distillation, column chromatography or other conventional method. The ester compound isolated may be used as a material for biochemical optical resolution. Hydrolysis of the ester compound with aqueous alkaline solution gives free acids which can be used as a material for optical resolution or as an intermediate for low-mammalian toxic insecticides.

According to the present process, trans-dihalo acid esters are obtained with high efficiency.

The present invention is explained in more detail by following examples.

Example 1

Titanium (IV) ethoxide (342 mg) was added under a nitrogen atmosphere to dichloro acid ethyl ester (5 g; cis, 57.6 %, trans 42.4 %) and the mixture was stirred for 10 minutes. Then, to the mixture was added lithium ethoxide (286 mg). The mixture was allowed to react at 140° C. for 4 hours with stirring.

Then, the mixture was cooled to room temperature, washed with water and subjected to distillation to obtain a fraction (4.81 g, a boiling point: 88°–90° C./1 mmHg). The fraction was identified as dichloro acid ethyl ester by IR spectrum.

Gas chromatographic analysis gave the following results: cis 24.2 %, trans 75.8 %.

Example 2

Titanium (IV) ethoxide (755 mg) was added under a nitrogen atmosphere to cis-dichloro acid ethyl ester (5 g; cis 96.4 %, trans 3.6 %) and the mixture was stirred for 10 minutes. Sodium ethoxide (861 mg) was added thereto subsequently. The mixture was allowed to react at 100 ° C. for 4 hours with stirring.

Then, the similar procedure to that in Example 1 was applied to until dichloro acid ethyl ester (4.2 g) was obtained.

Cis/trans ratio: cis 26.0 %, trans 74.0%.

Example 3

Example 2 was repeated except that titanium (IV) isopropoxide (1.49 g) in place of titanium (IV) ethoxide and sodium ethoxide (803 mg) were used and the mixture was stirred at 140 ° C. for 4 hours in place of 100° C. for 4 hours, thereby to obtain dichloro acid ethyl ester (4.05 g).

Cis/trans ratio: cis 29.7 %, trans 70.3 %.

Example 4

Example 1 was repeated except that titanium (IV) ethoxide (1.36 g) and sodium isopropoxide (1.56 g) in place of lithium ethoxide were used, thereby to obtain a mixture (4.22 g) of dichloro acid ethyl ester and dichloro acid isopropyl ester (65.3 : 36.5).

Cis/trans ratio: cis 19.5 %, trans 80.5 %.

Example 5

Example 1 was repeated except that titanium (IV) ethoxide (597 mg) and sodium methoxide (335 mg) in place of lithium ethoxide were used, thereby to obtain a mixture (4.32 g) of dichloro acid methyl ester and dichloro acid ethyl ester (11.8 : 88.2).

Cis/trans ratio: cis 38.9 %, trans 61.1 %.

Example 6

Example 1 was repeated except that dichloro acid methyl ester (5 g; cis 44.1 %, trans 55.9 %) in place of dichloro acid ethyl ester, titanium (IV) ethoxide (1.27 g) and lithium ethoxide (932 mg) were used, thereby to obtain a mixture (4.73 g) of dichloro acid methyl ester and dichloro acid ethyl ester (16 : 84).

Cis/trans ratio: cis 33 %, trans 67 %.

Example 7

Example 1 was repeated except that dichloro acid isopropyl ester (5 g; cis 96.6 %, trans 3.4 %) in place of dichloro acid ethyl ester, titanium (IV) ethoxide (455 mg) and lithium ethoxide (528 mg) were used, thereby to obtain a mixture (4.37 g) of dichloro acid ethyl ester and dichloro acid isopropyl ester (27.9 : 72.1).

Cis/trans ratio: cis 24.6 %, trans 75.4 %.

Example 8

Silicon tetraiodide (1.01 g) was added under a nitrogen atmosphere to a solution of dichloro acid ethyl ester (2.5 g; cis 57.6 %, trans 42.2 %) in chlorobenzene (10 g) and the mixture was stirred at 100° C. for 4 hours.

Then, the mixture was cooled to room temperature, washed with water and subjected to distillation to obtain a fraction (1.89 g, a boiling point: 88°–90 ° C./1 mmHg). The fraction was identified as dichloro acid ethyl ester by IR spectrum.

Gas chromatographic analysis gave the following results: cis 24.1 %, trans 75.9 %.

Example 9

Silicon tetraiodide (571 mg) and iodine (278 mg) were added under a nitrogen atmosphere to a solution of the same dichloro acid ethyl ester (2.5 g) as used in Example 8 in acetonitrile (22.5 g). The mixture was stirred at 80 ° C. for 4 hours.

Then, the mixture was cooled to room temperature, washed with a 2 % sodium thiosulfate aqueous solution (9 g) and washed with water. The organic layer obtained was distilled to give dichloro acid ethyl ester (2.25 g). Gas chromatographic analysis gave the following result: cis 15.5 %, trans 84.5 %.

Example 10

Example 9 was repeated except that stirring was made at 25° C. for 4 hours in place of 80° C. for 4 hours, thereby to obtain dichloro acid ethyl ester. Cis/trans ratio: cis 34.1 %, trans 65.9 %.

Example 11

Example 9 was repeated except that acetonitrile (15.4 g), silicon tetraiodide (503 mg) and iodine-monobromide (209 mg) in place of iodine were used and the mixture was stirred at 80° C. for 5 hours in place of 80° C. for 4 hours, thereby to obtain dichloro acid ethyl ester (1.94 g).

Cis/trans ratio: cis 23.9%, trans 76.1 %.

Example 12

Example 9 was repeated except that acetonitrile (13.5 g), silicon tetraiodide (582 mg) and iodine monochloride (183 mg) in place of iodine were used, thereby to obtain dichloro acid ethyl ester (1.86 g).

Cis/trans ratio: cis 21.2 %, trans 78.8 %.

Example 13

Example 9 was repeated except that dichlorobenzene (9.2 g) in place of acetonitrile, dichloro acid ethyl ester (2.5 g; cis 96.3 %, trans 3.7 %), silicon tetraiodide (579 mg) and iodine (259 mg) were used and the mixture was stirred at 50° C. for 6 hours in place of 80° C. for 4 hours, to obtain dichloro acid ethyl ester (1.97 g).

Cis/trans ratio: cis 17.8 %, trans 82.2 %.

Example 14

Example 9 was repeated except that dichloroethane (22.5 g) in place of acetonitrile, silicon tetraiodide (573 mg) and iodine (246 mg) were used, to obtain dichloro acid ethyl ester (2.01 g).

Cis/trans ratio: cis 18.6 %, trans 81.4 %.

Reference Example 1

Lithium ethoxide (263 mg) was added to the same dichloro acid ethyl ester (5 g) as used in Example 2 and the mixture was stirred at 140° C. for 4 hours.

Then, the similar procedure to that in Example 2 was applied to obtain dichloro chrysanthemic acid ethyl ester (4.75 g).

Cis/trans ratio: cis 95.8 %, trans 4.2 %.

Reference Example 2

Reference Example 1 was repeated except that sodium ethoxide (1.22 g) was used in place of lithium ethoxide to obtain a mixture (4.68 g) of dichloro chrysanthemic acid ethyl ester and 2,2-dimethyl-3-(2-chloroethynyl)-cyclopropane carboxylic acid ethyl ester (71.5 : 28.5).

Cis/trans ratio of dichloro acid ethyl ester: cis 25 %, trans 75 %.

We claim:

1. A process for preparing trans-2,2-dimethyl-3-(2,2-dihalovinyl)-cyclopropane carboxylic acid esters which comprises allowing either alkali metal alkoxides together with titanium alkoxides or silicon iodides to react with cis- or cis-/trans-mixed 2,2-dimethyl-3-(2,2-dihalovinyl)cyclopropane-cyclopropane carboxylic acid esters having the formula

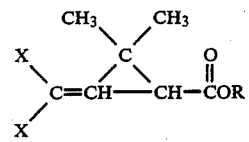

wherein X stands for a halogen atom and R stands for an alkyl, cycloalkyl or aralkyl group having 1–10 carbon atoms.

2. A process according to claim 1 wherein the reaction is conducted in the presence of the alkali metal alkoxides together with the titanium alkoxide.

3. A process according to claim 2 wherein the alkali metal alkoxides are present in an amount of 1/50–1 time as much as the dihalo acid esters in mole.

4. A process according to claim 2 wherein the alkali metal moiety of the alkali metal alkoxides is selected from the group consisting of lithium, sodium and potassium and alkoxide moiety of the alkali metal alkoxides is selected from the group consisting of methoxide, ethoxide, n-propoxide, isopropoxide, t-butoxide, sec-butoxide, isobutoxide, pentanoxide and hexanoxide.

5. A process according to claim 4 wherein the alkali metal alkoxides are lithium ethoxide, lithium propoxide, sodium ethoxide or sodium propoxide.

6. A process according to claim 2 wherein the titanium alkoxides are titanium methoxide, titanium ethoxide, titanium propoxide, titanium isopropoxide, titanium butoxide, titanium isobutoxide, titanium sec-butoxide or titanium t-butoxide.

7. A process according to claim 2 wherein the titanium alkoxides are present in an amount of 1/50–½ time as much as the dihalo acid esters in mole.

8. A process according to claim 2 wherein the process is conducted in the absence of solvents.

9. A process according to claim 2 wherein the reaction is conducted at 50–200 ° C.

10. A process according to claim 1 wherein the reaction is conducted in the presence of the silicon iodides.

11. A process according to claim 10 wherein the silicon iodides are present in an amount of 1/200–1 time as much as the dihalo acid esters in mole.

12. A process according to claim 10 wherein the silicon iodides are silicon tetraiodide.

13. A process according to claim 10 wherein the reaction is conducted in the presence of iodine-halides.

14. A process according to claim 13 wherein the iodine halides are iodine, iodine bromide or iodine chloride.

15. A process according to claim 13 wherein the iodine-halides are present in an amount of 1/200–1 time as much as the dihalo acid esters in mole.

16. A process according to claim 10 wherein the reaction is carried out at 0°–150 ° C.

17. A process according to claim 10 wherein the reaction is carried out in such solvents as aromatic hydrocarbons, halogenated hydrocarbons or nitriles.

* * * * *